(12) United States Patent
Cheng et al.

(10) Patent No.: US 11,867,506 B2
(45) Date of Patent: Jan. 9, 2024

(54) SCANNING DEVICE AND OPTICAL COHERENCE TOMOGRAPHY SYSTEM

(71) Applicant: Medimaging Integrated Solution, Inc., Hsinchu (TW)

(72) Inventors: Chu-Ming Cheng, Hsinchu (TW); Long-Sheng Liao, Hsinchu (TW)

(73) Assignee: MEDIMAGING INTEGRATED SOLUTION, INC., Hsinchu (TW)

( * ) Notice: Subject to any disclaimer, the term of this patent is extended or adjusted under 35 U.S.C. 154(b) by 0 days.

(21) Appl. No.: 17/186,677

(22) Filed: Feb. 26, 2021

(65) Prior Publication Data
US 2021/0333090 A1  Oct. 28, 2021

(30) Foreign Application Priority Data

Apr. 22, 2020 (TW) .................................. 109113537

(51) Int. Cl.
*G01B 9/02* (2022.01)
*G01B 9/02091* (2022.01)
*A61B 3/10* (2006.01)
*G02B 26/08* (2006.01)

(52) U.S. Cl.
CPC .......... *G01B 9/02091* (2013.01); *A61B 3/102* (2013.01); *G02B 26/0833* (2013.01)

(58) Field of Classification Search
CPC ............ G01B 9/02091; G01B 9/02029; G01B 9/0203; G01B 9/02063; A61B 3/102; A61B 3/12; A61B 3/14; A61B 5/0066; G02B 26/0833

See application file for complete search history.

(56) References Cited

U.S. PATENT DOCUMENTS

| | | | |
|---|---|---|---|
| 9,993,155 B2* | 6/2018 | Cheng | G02B 9/14 |
| 10,595,722 B1* | 3/2020 | Pascal | G01B 9/0203 |
| 2006/0256343 A1* | 11/2006 | Choma | A61B 5/0073 |
| | | | 356/450 |
| 2010/0118132 A1* | 5/2010 | Yumikake | G01B 9/0203 |
| | | | 348/78 |
| 2013/0194541 A1* | 8/2013 | Aoki | G01B 9/02089 |
| | | | 356/479 |
| 2013/0265547 A1* | 10/2013 | Higuchi | G01B 9/0203 |
| | | | 351/208 |
| 2014/0198299 A1* | 7/2014 | Cheng | A61B 3/0091 |
| | | | 351/205 |

(Continued)

FOREIGN PATENT DOCUMENTS

| | | |
|---|---|---|
| CN | 110755031 A | 2/2020 |
| WO | WO2019035441 A1 | 2/2019 |

*Primary Examiner* — Uzma Alam
*Assistant Examiner* — Jonathon Cook
(74) *Attorney, Agent, or Firm* — MUNCY, GEISSLER, OLDS & LOWE, P.C.

(57) ABSTRACT

A scanning device applied to an optical coherence tomography system integrates a scanning lens group required by the coherence tomography system into a fundus imaging system, so that the coherence tomography system and the fundus imaging system can share the scanning lens group for focusing. The above-mentioned scanning device can shorten a response time of focusing and reduce the volume of the system. An optical coherence tomography system including the above-mentioned scanning device is also disclosed.

16 Claims, 3 Drawing Sheets

(56) References Cited

U.S. PATENT DOCUMENTS

| | | | |
|---|---|---|---|
| 2014/0198300 A1* | 7/2014 | Goto | G01B 9/02044 |
| | | | 351/246 |
| 2016/0183785 A1* | 6/2016 | Iwase | A61B 3/14 |
| | | | 351/246 |
| 2016/0235299 A1* | 8/2016 | Yamamoto | A61B 3/102 |
| 2020/0196857 A1* | 6/2020 | Orlowski | A61B 3/0025 |

* cited by examiner

SCANNING DEVICE AND OPTICAL COHERENCE TOMOGRAPHY SYSTEM

BACKGROUND OF THE INVENTION

1. Field of the Invention

The present invention relates to a scanning device and an optical coherence tomography system, particularly to an optical coherence tomography system integrated with an optical camera.

2. Description of the Prior Art

The optical coherence tomography (OCT) is an optical imaging technology, wherein two light beams are respectively reflected by a reference arm and a sample arm to interfere mutually on an optical detector to form a tomographic image.

Refer to FIG. 1 for a conventional optical coherence tomography system used to obtain tomographic fundus images. The system comprises a scanning light source 11, a coupler 12, a reference arm 13, a sample arm 14, and a spectrometer 15. Through optical fibers 121, the coupler 12 is optically coupled to the scanning source 11, the reference arm 13, the sample arm 14 and the spectrometer 15. The coupler 12 splits the scanning light into two light beams to respectively enter the reference arm 13 and the sample arm 14. The reference light beam RL, which enters the reference arm 13, is output by a collimator 131, reflected by a reference reflecting mirror 132 to go back to the collimator 131 and then return to the coupler 12. The sampling light beam SL, which enters the sample arm 14, is output by a collimator 141 to pass through a scanning reflecting mirror 142, a scanning lens 143, a light splitter 144 and an objective lens 145 and then reach a fundus of an eyeball 300 of a testee. The light beam reflected from the fundus of the eyeball 300 returns to the collimator 141 along the same path and then returns to the coupler 12. The spectrometer 15 detects the light signal generated by the interference of the reference light beam RL and the sampling light beam SL for the succeeding reconstruction process to form a fundus tomographic image.

Refer to FIG. 1 again. In order to capture the fundus image of the eyeball 300, the sample arm 14 further comprises a fundus imaging system 16, whereby the operator can observe the fundus position of the testee and confirm the position where OCT is to scan. An illumination light beam reflected by the fundus of the eyeball 300 travels trough the objective lens 145, the light splitter 144, a focusing lens 161 and an imaging lens 162 along an optical axis OA to form am image on an image sensor 163, whereby a fundus image of the eyeball 300 is generated.

It is easily understood: the eyeballs 300 of testees respectively have their diopters because of such as myopia and hyperopia. In order to obtain better tomographic images, the scanning lens 143 may be moved to compensate for the diopter of an eyeball. Similarly, in order to acquire better fundus images, the focusing lens 161 of the fundus imaging system 16 may be moved to compensate for the diopter of an eyeball. However, different focusing systems respectively need corresponding control devices. The abovementioned measures not only increase the time and cost of focusing but also impair the miniaturization of optical coherence tomography systems. Thus, the application of the optical coherence tomography systems is limited.

Accordingly, it is a target the manufacturers desire to achieve to provide a fast-focusing and compact optical coherence tomography system.

SUMMARY OF THE INVENTION

The present invention provides a scanning device and an optical coherence tomography system, wherein a scanning lens group, which an optical coherence tomography system needs, is integrated into a fundus imaging system, whereby the optical coherence tomography system and the fundus imaging system can share the same scanning lens group in focusing, whereby to shorten the response time of focusing and reduce the volume of the system.

In one embodiment, the scanning device of the present invention is integrated with a main structure to form an optical coherence tomography system, wherein the main structure outputs a sampling light beam. The scanning device comprises a scanning reflector, a light splitter, a scanning lens group, an objective lens, an illumination light source, an imaging lens group and an image sensor. The scanning reflector is optically coupled to the main structure to turn the direction of the sampling light beam and make the sampling light beam scan the fundus of an eyeball. The light splitter is optically coupled to the scanning reflector to guide the sampling light beam to the eyeball. The scanning lens group is optically coupled to the light splitter. The objective lens and the scanning lens group are coaxially disposed with respect to an optical axis, whereby the sampling light beam coming from the light splitter passes through the scanning lens group and the objective lens and then reaches the fundus of the eyeball. The sampling light beam reflected from the fundus returns to the main structure along the same path to generate a corresponding optical coherence tomography image. The illumination light source is deposed at a position away from the optical axis and generates an illumination light beam, wherein the illumination light beam passes through the objective lens to illuminate the fundus. The imaging lens group is optically coupled to the light splitter. The image sensor is disposed at a light-exit side of the imaging lens group. The illumination light source, the objective lens, the scanning lens group, the imaging lens group and the image sensor jointly form a fundus imaging system. The optical coherence tomography system and the fundus imaging system share the same scanning lens group. Thereby, the illumination light beam reflected by the fundus of the eyeball passes through the objective lens, the scanning lens group, the light splitter, and the imaging lens group and then reaches the image sensor. Thus, an image of the fundus is generated in the image sensor.

In another embodiment, the optical coherence tomography system of the present invention comprises a main structure and a scanning device. The main structure includes a scanning light source, a coupler, and a spectrometer. The scanning light source generates a scanning light beam. The coupler is optically coupled to the scanning light source and divides the scanning light beam into a reference light beam and a sampling light beam. The reference light beam, which passes through a reference optical path, is reflected by a reference reflector and then goes along the reference optical path back to the coupler. The spectrometer is optically coupled to the coupler. The scanning device includes a scanning reflector, a light splitter, a scanning lens group, an objective lens, an illumination light source, an imaging lens group and an image sensor. The scanning reflector is optically coupled to the coupler to turn the direction of the sampling light beam and make the sampling light beam scan the fundus of an eyeball. The light splitter is optically coupled to the scanning reflector to guide the sampling light beam to the eyeball. The scanning lens group is optically coupled to the light splitter. The objective lens and the scanning lens group are coaxially disposed with respect to an optical axis, whereby the sampling light beam coming the light splitter passes through the scanning lens group and the objective lens and then reaches the fundus of the eyeball. The sampling light beam reflected from the fundus returns to the coupler along the same path. The spectrometer receives the reference light beam reflected from the reference reflector and the sampling light beam reflected from the fundus and generates a corresponding tomographic image. The illumination light source is deposed at a position away from the optical axis and generates an illumination light beam, wherein the illumination light beam passes through the objective lens to illuminate the fundus. The imaging lens group is optically coupled to the light splitter. The image sensor is disposed at a light-exit side of the imaging lens group. The illumination light source, the objective lens, the scanning lens group, the imaging lens group and the image sensor jointly form a fundus imaging system. The optical coherence tomography system and the fundus imaging system share the same scanning lens group. Thereby, the illumination light beam reflected by the fundus of the eyeball passes through the objective lens, the scanning lens group, the light splitter, and the imaging lens group and then reaches the image sensor. Thus, an image of the fundus is generated in the image sensor.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENTS

Various embodiments of the present invention will be described in detail below and illustrated in conjunction with the accompanying drawings. In addition to these detailed descriptions, the present invention can be widely implemented in other embodiments, and apparent alternations, modifications and equivalent changes of any mentioned embodiments are all included within the scope of the present invention and based on the scope of the Claims. In the descriptions of the specification, in order to make readers have a more complete understanding about the present invention, many specific details are provided; however, the present invention may be implemented without parts of or all the specific details. In addition, the well-known steps or elements are not described in detail, in order to avoid unnecessary limitations to the present invention. Same or similar elements in Figures will be indicated by same or similar reference numbers. It is noted that the Figures are schematic and may not represent the actual size or number of the elements. For clearness of the Figures, some details may not be fully depicted.

Figure 1:
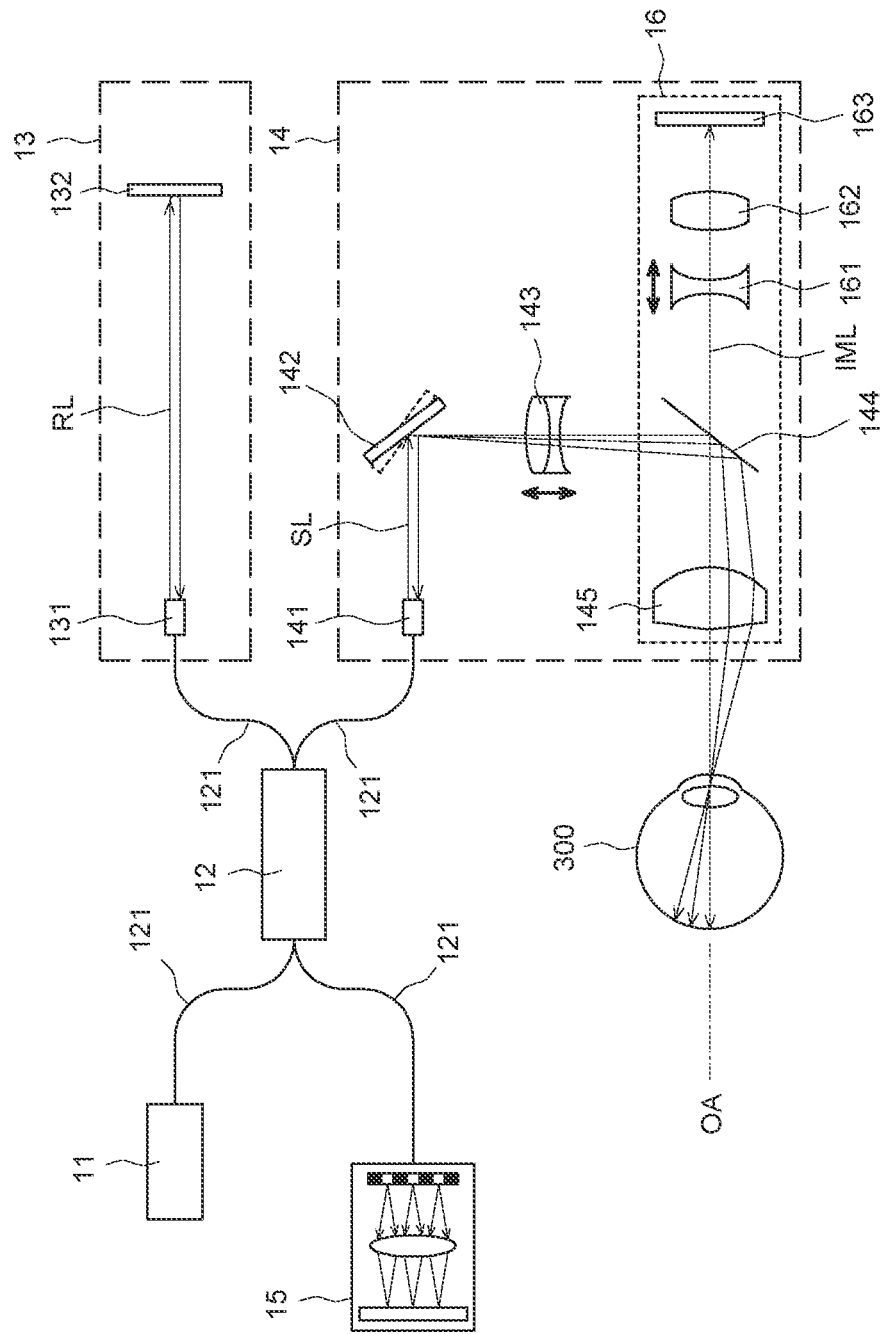
FIG. 1 is a diagram schematically showing a conventional optical coherence tomography system.
Figure 2:
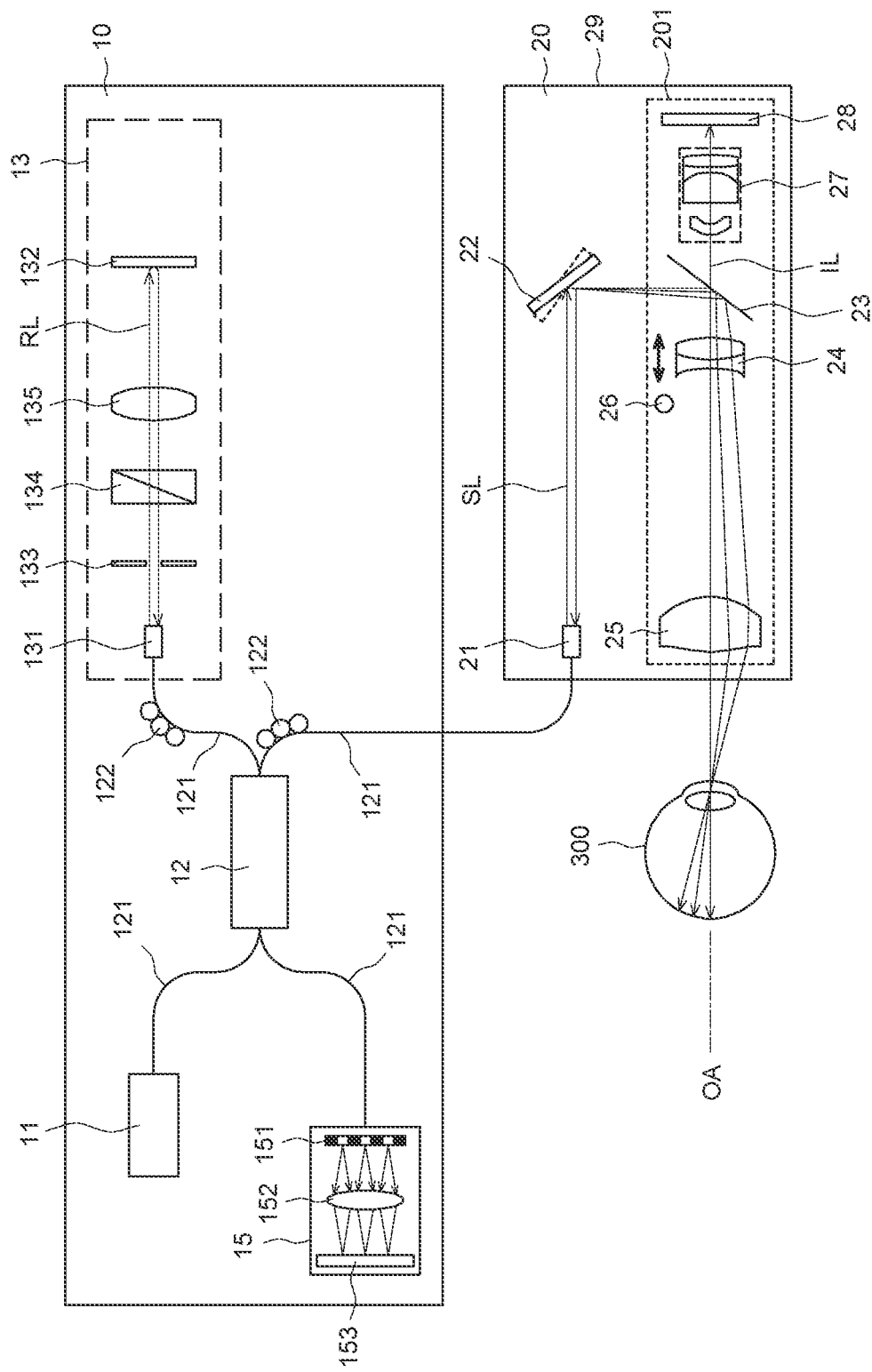
FIG. 2 is a diagram schematically showing an optical coherence tomography system according to one embodiment of the present invention.

Refer to FIG. 2. In one embodiment, the optical coherence tomography system of the present invention comprises a main structure 10 and a scanning device 20. The main structure 10 includes a scanning light source 11, a coupler 12, and a spectrometer 15. The scanning light source 11 generates a scanning light beam. For example, the scanning light source 11 may be a superluminescent diode. The coupler 12 is optically coupled to the scanning light source 11 and divides the scanning light beam into a reference light beam RL and a sampling light beam SL. The reference light beam RL and the sampling light beam SL are respectively guided to a reference arm 13 and a sample arm (i.e. the scanning device 20). For example, the coupler 12 is optically coupled to the scanning light source 11 via an optical fiber 121 and respectively outputs the reference light beam RL and the sampling light beam SL to the reference arm 13 and the sample arm (the scanning device 20) via the optical fibers 121.

In one embodiment, the reference arm 13 at least includes a collimator 131 and a reference reflector 132. The collimator 131 is disposed at one end of the optical fiber 121. The reference light beam RL is output from the collimator 131, going through a reference optical path to the reference reflector 132, and then reflected by the reference reflector 132 back to the collimator 131. It is easily understood: the reference arm 13 may also includes other suitable elements. For example, an aperture 133, a dispersion compensator (DC) 134, and a lens 135 may be disposed in the reference optical path to stabilize the quality of the reference light beam RL. The reference optical path is the path where the reference light beam RL is output by the coupler 12 and then reflected by the reference reflector 132 back to the coupler 12. The detailed structure of the reference arm 13 is well known by the persons skilled in the art and will not repeat herein. In one embodiment, the main structure 10 includes at least one polarization controller 122. The polarization controllers 122 are optically coupled to the coupler 12 and used to polarize the light beams going to the reference arm 13 and the sample arm (the scanning device 20).

The spectrometer 15 is optically coupled to the coupler 12. For example, the spectrometer 15 is optically coupled to the coupler 12 via the optical fiber 121. The spectrometer 15 receives the light signals returned by reference arm 13 and the sample arm (the scanning device 20). In one embodiment, the spectrometer 15 includes a diffraction grating 151, a lens 152 and a line scan camera 153, whereby to detect the light signals generated by the interference of the reference light beam RL and the sampling light beam SL respectively returned by the reference arm 13 and the sample arm (the scanning device 20).

The scanning device 20 includes a scanning reflector 22, a light splitter 23, a scanning lens group 24, an objective lens 25, an illumination light source 26, an imaging lens group 27, and an image sensor 28. In one embodiment, the scanning device 20 further includes an optical fiber 121 and a collimator 21. One end of the optical fiber 121 is optically coupled to the coupler 12 of the main structure 10. The collimator 21 is disposed at another end of the optical fiber 121 and optically coupled to the scanning reflector 22. Hence, the sampling light beam SL is output by the collimator 21 to the scanning reflector 22, and the scanning reflector 22 may deflect the path of the scanning light beam SL via rotation or another measure. Thereby, the position where the sampling light beam SL illuminates the fundus of the eyeball 300 may be varied. It is easily understood: a complete scanning of a specified area of the fundus of the eyeball 300 can be realized via changing the position illuminated by the sampling light beam SL in sequence.

The light splitter 23 is optically coupled to the scanning reflector 22 and guides the sampling light beam SL to project to the direction of the eyeball 300. The scanning lens group 24 is optically coupled to the light splitter 23, and the objective lens 25 and the scanning lens group 24 disposed coaxially with respect to an optical axis OA, whereby the sampling light beam SL coming from the light splitter 23 passes through the scanning lens group 24 and the objective lens 25 in sequence and then reaches the fundus of the eyeball 300. The sampling light beam SL reflected from the fundus of the eyeball 300 passes through the objective lens 25, the scanning lens group 24, and the light splitter 23 in sequence to reach the scanning reflector 22; then, the scanning reflector 22 reflects the scanning light beam SL back to the collimator 21. In brief, the sampling optical path starts from the coupler 12 outputting the sampling light beam SL to the fundus of the eyeball 300 reflecting the sampling light beam SL and then returns from the fundus of the eyeball 300 back to the coupler 12. After the reference light beam RL reflected from the reference reflector 132 and the sampling light beam SL reflected from the fundus of the eyeball 300 both return to the coupler 12, the coupler 12 further outputs the reference light beam RL and the sampling light beam SL to the spectrometer 15. The spectrometer 15 detects the light signal generated by the interference of the reference light beam RL and the sampling light beam SL for the succeeding reconstruction process to form a fundus tomographic image.

The scanning reflector 22, the light splitter 23, the scanning lens group 24, the objective lens 25, the illumination light source 26, the imaging lens group 27, and the image sensor 28 of the scanning device 20 jointly form a fundus imaging system 201. The illumination light source 26 is disposed at a position away from the optical axis OA and generates an illumination light beam. The illumination light beam is converged by the objective lens 25 and then passes the pupil of the eyeball 300 to illuminate the fundus. For example, the illumination light source 26 may be a point-like light source, such a light emitting diode. In one embodiment, the illumination light beam generated by the illumination light source 26 is directly projected to the objective lens 25, whereby reflectors and relay lenses are saved and the volume of the system is reduced.

The imaging lens group 27 is optically coupled to the light splitter 23, and the image sensor 28 is disposed at a light-exit side of the imaging lens group 27. Thus, the illumination light beam IL reflected from the fundus of the eyeball 300 passes through the objective lens 25, the scanning lens group 24, the light splitter 23 and the imaging lens group 27 in sequence to reach the image sensor 28 to generate a corresponding fundus image. It should be explained herein: the lenses shown in FIG. 2, such as the objective lens 25, the scanning lens group 24 and the imaging lens group 27, are only exemplifications to facilitate description and discussion. The optical characteristics thereof should be designed according to practical requirement.

Figure 3:
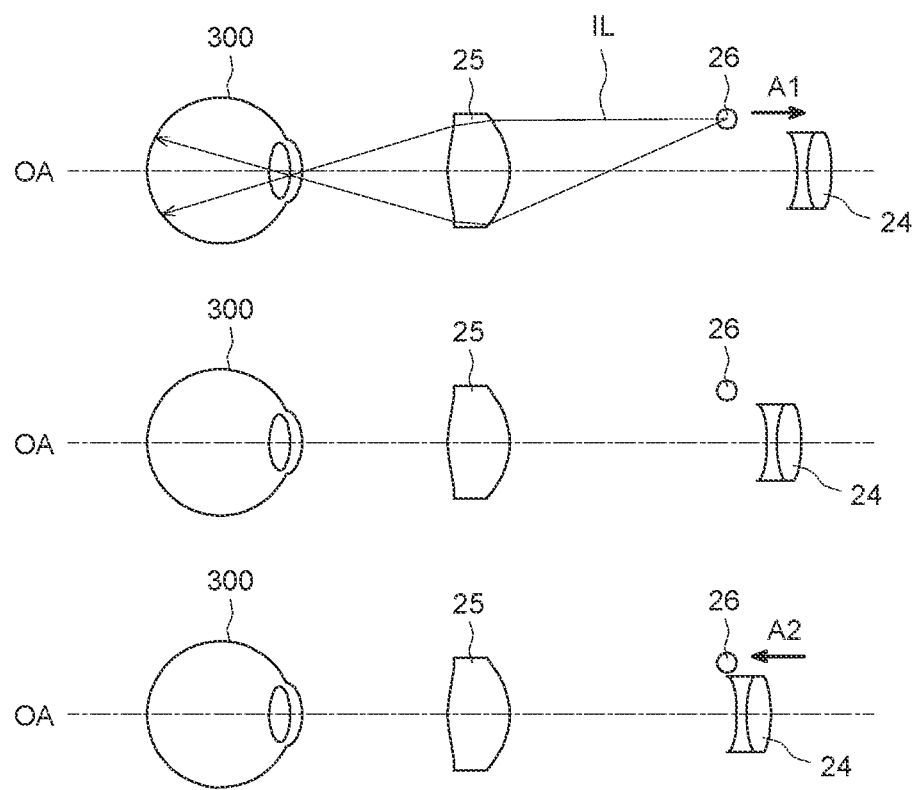
FIG. 3 is a diagram schematically showing focusing operations of an optical coherence tomography system according to one embodiment of the present invention.

In the structure shown in FIG. 2, the scanning lens group 24 required by the optical coherence tomography system is incorporated into the fundus imaging system 201. Therefore, the focal length may be adjusted to compensate for different diopters of different eyeballs 300 and acquire better tomographic images and fundus images via merely moving the scanning lens group 24 along the optical axis OA. In other words, the optical coherence tomography system and the fundus imaging system 201 can share the same scanning lens group 24 in focusing. Therefore, while the operator completes the focusing of the fundus imaging system 201, the focusing of the optical coherence tomography system is also completed. Refer to FIG. 3. While the eyeball 300 of a testee has normal vision, the scanning lens group 24 is located at a preset position, as shown in the middle drawing of FIG. 3. While the eyeball 300 of a testee has hyperopia (+10D), the scanning lens group 24 is moved along the optical axis OA toward a direction far away from the objective lens 25, as shown by the arrow A1 in the upper drawing of FIG. 3. While the eyeball 300 of a testee has myopia (−10D), the scanning lens group 24 is moved along the optical axis OA toward a direction approaching the objective lens 25, as shown by the arrow A2 in the lower drawing of FIG. 3.

In one embodiment, the illumination light source 26 and the imaging lens group 27 are fixed, and only the scanning lens group 24 is moved during the focusing process. In other words, the distance of the illumination light source 26 to the objective lens 25 and the distance of the imaging lens group 27 to the objective lens 25 are unchanged. Thereby, the optical design is simplified. In one embodiment, the distance of the illumination light source 26 to the objective lens 25 is smaller than or equal to the distance of the scanning lens group 24 to the objective lens 25. It should be noted: the focal length is adjusted via moving the scanning lens group 24 in the embodiment shown in FIG. 3. However, the present invention is not limited by this embodiment. In another embodiment, the focal length may be adjusted via varying the curvature of the scanning lens group 24.

According to the abovementioned structure, the optical coherence tomography system of the present invention can adjust the focal length merely using a set of control device corresponding to the scanning lens group 24. Therefore, the present invention simplifies the optical path design and thus uses fewer elements and saves much cost. Further, the present invention can significantly shorten the time of focusing and effectively reduce the volume of the system. Hence, the present invention favors miniaturization and portability of the scanning device. Refer to FIG. 2 again. The scanning device 20 may further include a handheld housing 29; the scanning reflector 22, the light splitter 23, the scanning lens group 24, the objective lens 25, the illumination light source 26, the imaging lens group 27 and the image sensor 28 are all disposed inside the handheld housing 29. The scanning device 20 is optically coupled to the main structure 10 via an optical fiber 121. Thus, the operator may hold the scanning device 20 to perform inspection. Therefore, the present invention is very convenient to inspect the fundus of the persons hard to move (such as the patients unable to get out of bed), infants, or animals.

In one embodiment, the scanning device 20 may be optically and electrically coupled to the main structure 10 in a detachable way. For example, the main structure 10 includes an optical fiber connection port and an electric connection port; the scanning device 20 includes an optical fiber plug and an electric plug respectively corresponding to the optical fiber connection port and the electric connection port of the main structure 10, whereby different scanning devices 20 may be coupled to the same main structure 10 for different applications or different testees.

In conclusion, the present invention provides a scanning device and an optical coherence tomography system, wherein the scanning lens group required by the optical tomography system is incorporated into a fundus imaging system, whereby the optical coherence tomography system and the fundus imaging system can share the same scanning lens group and use the scanning lens group in focusing. Therefore, the present invention not only can simplify design but also can reduce cost. Further, the present invention can shorten the time of focusing and reduce the volume of the system.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

What is claimed is:

1. A scanning device, which cooperates with a main structure to form an optical coherence tomography system, wherein the main structure outputs a sampling light beam, and the scanning device comprises:
   a scanning reflector, optically coupled to the main structure, and deflecting the sampling light beam to make the sampling light beam scan a fundus of an eyeball;
   a light splitter, optically coupled to the scanning reflector, and guiding the sampling light beam to the eyeball;
   a scanning lens group, optically coupled to the light splitter;
   an objective lens, disposed coaxially with the scanning lens group with respective to an optical axis, and making the sampling light beam, which comes from the light splitter and passes through the scanning lens group and the objective lens in sequence, reach the fundus of the eyeball, wherein the sampling light beam reflected from the fundus returns to the main structure along a sampling optical path to generate an optical tomographic image;
   an illumination light source, disposed at a position away from the optical axis, and generating and projecting an illumination light beam to the objective lens, the objective lens converges the illumination light beam to illuminate the fundus, and an optical path of the illumination light beam is axially separate from the optical axis of the sampling light beam between the scanning lens group and the objective lens;
   an imaging lens group, optically coupled to the light splitter;
   an image sensor, disposed at a light-exit side of the imaging lens group, wherein the illumination light source, the objective lens, the scanning lens group, the imaging lens group and the image sensor jointly form a fundus imaging system, and wherein the optical coherence tomography system and the fundus imaging system share the scanning lens group, and wherein the illumination light beam reflected from the fundus goes through the objective lens, the scanning lens group, the light splitter, and the imaging lens group to the image sensor to generate a corresponding fundus image; and
   a handheld housing,
   wherein the scanning reflector, the light splitter, the scanning lens group, the objective lens, the illumination light source, the imaging lens group and the image sensor are disposed inside the handheld housing, and wherein the scanning device is optically coupled to the main structure via an optical fiber,
   wherein a distance of the illumination light source to the objective lens is smaller than or equal to a distance of the scanning lens group to the objective lens, and
   wherein the imaging lens group is spatially located between the light splitter and the image sensor.

2. The scanning device according to claim 1, wherein a focal length is adjusted via moving the scanning lens group along the optical axis or varying a curvature of the scanning lens group.

3. The scanning device according to claim 1 further comprising a collimator optically coupled to the scanning reflector,
   wherein the main structure and the collimator are respectively disposed at two ends of the optical fiber.

4. The scanning device according to claim 1, wherein the illumination light source is a point-like light source.

5. The scanning device according to claim 1, wherein a distance of the illumination light source to the objective lens is a fixed value.

6. The scanning device according to claim 1, wherein a distance of the imaging lens group to the objective lens is a fixed value.

7. An optical coherence tomography system comprising:
   a main structure comprising:
   a scanning light source, generating a scanning light beam;
   a coupler, optically coupled to the scanning light source, dividing the scanning light beam into a reference light beam and a sampling light beam, wherein the reference light beam traveling along a reference optical path is reflected by a reference reflector to return to the coupler along the reference optical path; and
   a spectrometer, optically coupled to the coupler; and
   a scanning device, comprising:
   a scanning reflector, optically coupled to the coupler, and deflecting the sampling light beam to make the sampling light beam scan a fundus of an eyeball;
   a light splitter, optically coupled to the scanning reflector, and guiding the sampling light beam to the eyeball;
   a scanning lens group, optically coupled to the light splitter;
   an objective lens, disposed coaxially with the scanning lens group with respective to an optical axis, and making the sampling light beam, which comes from the light splitter and passes through the scanning lens group and the objective lens in sequence, reach the fundus of the eyeball, wherein the sampling light beam reflected from the fundus returns to the coupler along a sampling optical path, and wherein the spectrometer receives the reference light beam reflected from the reference reflector and the sampling light beam reflected from the fundus to generate an optical tomographic image;
   an illumination light source, disposed at a position away from the optical axis, and generating and projecting an illumination light beam to the objective lens, the objective lens converges the illumination light beam to illuminate the fundus, and an optical path of the illumination light beam is axially separate from the optical axis of the sampling light beam between the scanning lens group and the objective lens;
   an imaging lens group, optically coupled to the light splitter;
   an image sensor, disposed at a light-exit side of the imaging lens group, wherein the illumination light source, the objective lens, the scanning lens group, the imaging lens group and the image sensor jointly form a fundus imaging system, and wherein the optical coherence tomography system and the fundus imaging system share the scanning lens group, and wherein the illumination light beam reflected from the fundus goes through the objective lens, the scanning lens group, the light splitter, and the imaging lens group to the image sensor to generate a corresponding fundus image; and a handheld housing, wherein the scanning reflector, the light splitter, the scanning lens group, the objective lens, the illumination light source, the imaging lens group and the image sensor are disposed inside the handheld housing, and wherein the scanning reflector is optically coupled to the coupler via an optical fiber, wherein a distance of the illumination light source to the objective lens is smaller than or equal to a distance of the scanning lens group to the objective lens, and wherein the imaging lens group is spatially located between the light splitter and the image sensor.

8. The optical coherence tomography system according to claim 7, wherein the scanning light source comprises a superluminescent diode.

9. The optical coherence tomography system according to claim 7, wherein the spectrometer comprises a diffraction grating and a line scan camera.

10. The optical coherence tomography system according to claim 7, wherein the main structure further comprises:

at least one polarization controller, optically coupled to the coupler and used to polarize the reference light beams and the sampling light beam.

11. The optical coherence tomography system according to claim 7, wherein a focal length is adjusted via moving the scanning lens group along the optical axis or varying a curvature of the scanning lens group.

12. The optical coherence tomography system according to claim 7, wherein the scanning device further comprises a collimator optically coupled to the scanning reflector, wherein the main structure and the collimator are respectively disposed at two ends of the optical fiber.

13. The optical coherence tomography system according to claim 7, wherein the scanning device is optically and electrically coupled to the main structure in a detachable way.

14. The optical coherence tomography system according to claim 7, wherein the illumination light source is a point-like light source.

15. The optical coherence tomography system according to claim 7, wherein a distance of the illumination light source to the objective lens is a fixed value.

16. The optical coherence tomography system according to claim 7, wherein a distance of the imaging lens group to the objective lens is a fixed value.

* * * * *